United States Patent
Di Mino et al.

(10) Patent No.: US 6,210,321 B1
(45) Date of Patent: Apr. 3, 2001

(54) ELECTRONIC STIMULATION SYSTEM FOR TREATING TINNITUS DISORDERS

(75) Inventors: Alfonso Di Mino; Andre Di Mino, both of Woodcliff Lake, NJ (US)

(73) Assignee: ADM Tronics Unlimited, Inc., Northvale, NJ (US)

( * ) Notice: Subject to any disclaimer, the term of this patent is extended or adjusted under 35 U.S.C. 154(b) by 0 days.

(21) Appl. No.: 09/363,475

(22) Filed: Jul. 29, 1999

(51) Int. Cl.[7] .............................. H04R 25/00; A61H 1/00
(52) U.S. Cl. ................................. 600/28; 600/25
(58) Field of Search .............................. 600/25–28, 559; 607/55–57; 601/47; 128/748, 897; 604/36; 381/68–68.3

(56) References Cited

U.S. PATENT DOCUMENTS

| | | | |
|---|---|---|---|
| 3,764,748 | * 10/1973 | Branch et al. | 607/57 |
| 5,788,656 | * 8/1998 | Di Mino | 601/47 |
| 5,795,287 | * 8/1998 | Ball et al. | 600/25 |
| 5,800,336 | * 9/1998 | Ball et al. | 600/25 |

\* cited by examiner

*Primary Examiner*—Samuel G. Gilbert
(74) *Attorney, Agent, or Firm*—Hopgood, Calimafde, Judlowe & Mondolino

(57) ABSTRACT

An electronic stimulation system for treating a patient suffering from a tinnitus disorder in which the patient hears ringing or other sounds originating in the ear. The system includes an electrodynamically-actuated diaphragm and probe assembly acting as an applicator to which is applied a complex signal in the sonic range to cause the probe to vibrate in accordance with the signal and the diaphragm to audibly reproduce the signal. The probe is placed at a site on the patient in proximity to the cochlea of the inner ear whereby the probe vibrations are transmitted to the cochlea to stimulate this organ and thereby alleviate the tinnitus disorder. Because the patient who hears the internally-generated tinnitus sounds, also hears the reproduced complex signal he is able to adjust the generator of the complex signal so that its frequency components act to mask the frequencies of the tinnitus sounds.

10 Claims, 2 Drawing Sheets

ELECTRONIC STIMULATION SYSTEM FOR TREATING TINNITUS DISORDERS

BACKGROUND OF INVENTION

1. Field of Invention

This invention relates generally to the treatment of tinnitus disorders, and in particular to an electronic stimulation system in which a complex signal in the sonic range is applied to an electrodynamically-actuated diaphragm and probe assembly, acting as an applicator, to cause the probe to vibrate in accordance with the signal and to cause the diaphragm to audibly reproduce the signal. The vibrations of the probe are transmitted to the cochlea of the inner ear of the patient to mask internal tinnitus sounds heard by the patient.

2. Status of Prior Art

The human ear functions as an auditory system for converting incoming sound vibrations into electrical energy which triggers nerve impulses in the auditory nerve connected to the brain. In this auditory system, sounds picked up by the outer ear (auriole) are conducted through an auditory canal to a tympanic membrane or eardrum. The middle ear which is separated from the outer ear by the eardrum, contains three small bones which as sounds strike the eardrum are then caused to vibrate. These bone vibrations set up corresponding vibrations in an oval window from which the vibrations are conveyed to the three fluid-filled canals contained in the cochlea of the inner ear.

At the base of the central canal of the cochlea is a basilar membrane, and supported on this membrane is the organ of Corti and its hair cells. These cells are the true receptors of hearing, for proliferations from the fibers of the auditory nerve extend up the center of the cochlea and connect with these hair cells.

Auditory sounds vary in frequency throughout the audio spectrum. The ability to hear many different frequencies as distinct pitches is related to the ability of the cochlea to resolve these frequencies. In the range of about 200 to 2000 Hz this resolution is effected by differential response of the basilar membrane. The cochlea has different resonance values at different points along its length. Hence high tones cause the fluid of the cochlea and the membrane to vibrate near the base, while low tones cause these to vibrate near the apex.

The concern of the present invention is with the treatment of tinnitus disorders. Tinnitus aureum, in Latin, literally means "ringing of the ears" and is a common symptom in adults. Though the term refers to sounds originating in the ear, they may not be ringing in nature, for buzzing, humming, whistling and roaring sounds are also indicative of a tinnitus disorder.

A more precise definition of tinnitus is any sound sensation for which there is no source outside of the individual. According to the text Principles of Neurology by Adams & Victor-McGraw Hill (Third Edition). "For most forms of tinnitus, there is little effective treatment." Yet despite this negative approach to tinnitus, the prior art discloses various attempts to overcome this condition.

Thus the Westerman U.S. Pat. No. 5,325,872 (1994) discloses an electronic system for treating tinnitus in which the outputs of two voltage-controlled oscillators operating in the sonic range are combined and amplified. The resultant signal is applied to an ear piece placed on the outer ear of the patient. Hence what the patient hears is a therapeutic tone whose frequency repeatedly and slowly scans throughout a frequency range which contains the tinnitus ringing tone. According to Westerman, because the therapeutic tone with each scan repeats the ringing frequency, this acts to mask or suppress the ringing frequency.

A similar approach is taken by Gooch in U.S. Pat. No. 5,403,262 (1996) in which applied to the ear of a patient suffering from a tinnitus ringing sound is a tone of a frequency which masks the tinnitus ringing sound and overrules this sound.

The effectiveness of these prior approaches is believed to be of limited value in the treatment of tinnitus in that the therapeutic tones are applied to the outer ear of the nerve cells responsible for the tinnitus condition.

In the nerve center associated with the brain which is responsible for processing sounds, each individual nerve cell located in the uppermost level of the eight cranial nerve is stimulated only by a sound having a specific frequency. It is therefore the task of the multitude of nerve cells in the uppermost level of the eigth nerve to inform the brain that specific sounds or tones are being heard, or that a complex tone or a mixture of sounds are being heard. Hence each nerve cell in the nerve center has an assigned task.

The reason therefore a patient suffering from tinnitus has the sensation of hearing a ringing tone made up of specific frequencies is that the nerve cells that normally hear and transmit to the brain a really audible tone composed of these frequencies are being artificially stimulated, and may remain in this condition for a prolonged period. The cause of this faulty stimulation is not known. But what is known is that a substantial percentage of adults throughout the world suffer from tinnitus.

Inasmuch as the nerve center associated with the brain is the source of tinnitus disorders, and in the human auditory system, it is the cochlea that conducts impulses to this nerve center, in a system in accordance with the invention to treat tinnitus, it is the cochlea that is stimulated.

Our prior Di Mino patent 5,788,656 discloses an electronic stimulation system for treating a patient suffering from a tinnitus disorder; the system acting to transmit vibrations in the sonic range to the cochlea of the inner ear. The system includes an electromagnetically-actuated probe to which is applied a complex signal in the auditory range to cause the probe to vibrate in accordance with the signal, the probe being placed at a position on the patient in proximity to the cochlea of the inner ear whereby the probe vibrations are transmitted to the cochlea.

The mechanical vibrations conveyed by the probe in accordance with the complex signal in the sonic range actuating the probe must be properly related to the internal tinnitus sounds being heard by the patient being treated. It is only when this proper relationship exists, that the tones produced externally by the complex signal acts to mask and in time suppress the internal tinnitus sounds.

In the system disclosed in the prior Di Mino patent, the complex signal actuating the probe is generated by two audio-frequency oscillators, one operating in a low-frequency range whose upper limit is 400 Hz, the other in a higher frequency range whose upper limit is 1000 Hz. The resultant complex signal therefore includes the negative and positive beats of the two oscillator frequencies.

It is only the patient being treated who hears the internally-generated tinnitus sounds. In order therefore to produce a complex signal which is appropriate to an existing tinnitus condition and functions to mask the tinnitus sounds, it is the patient hearing the tinnitus sounds who must determine which complex signal is effective in treating his condition.

In order therefore for a system of the type disclosed in our prior Di Mino patent to be effective, it is essential that the two oscillators which together generate the complex signal be adjusted so that the resultant vibrations of the probe applied to the cochlea of the patient's ear then act to mask the internally-generated tinnitus sounds heard by the patient being treated.

But for the patient to be able to properly adjust the two oscillators, the complex signal must be reproduced so that it can be clearly heard by the patient. Then as the patient adjusts the oscillators, he can hear the resultant complex signal and determine which form of complex signal acts to effectively mask the internally-generated tinnitus sounds.

The practical drawback of the system disclosed in the Di Mino patent is that it does not adequately audibly reproduce the complex signal, and the patient therefore may have difficulty in adjusting the oscillators to generate the particular complex signal which is most effective in masking the tinnitus sounds.

SUMMARY OF INVENTION

In view of the foregoing, the main object of this invention is to provide an electronic stimulation system for treating a patient suffering from a tinnitus disorder; the system acting to convey vibrations in the sonic range to the cochlea of the inner ear.

More particularly, an object of this invention is to provide a system of the above type which includes an electrodynamically-actuated probe and diaphragm assembly to which is applied a complex signal in the auditory range to cause the probe to vibrate in accordance with the signal, the probe being placed at a position on the patient in proximity to the cochlea of the inner ear whereby the probe vibrations are transmitted to the cochlea.

A significant feature of the invention resides in a diaphragm and probe assembly which acts as an applicator whereby when the probe is placed behind the earlobe of the patient in proximity to the cochlea to transmit vibrations thereto in accordance with the complex signal, this signal is at the same time audibly reproduced. Hence the patient hearing the complex signal can then adjust the generator producing the complex signal so that it becomes effective in masking the tinnitus sounds he is hearing.

Briefly stated, these objects are accomplished by an electronic stimulation system for treating a patient suffering from a tinnitus disorder in which the patient hears ringing or other sounds originating in the ear. The system includes an electrodynamically-actuated diaphragm and probe assembly acting as an applicator to which is applied a complex signal in the sonic range to cause the probe to vibrate in accordance with the signal and the diaphragm to audibly reproduce the signal. The probe is placed at a site on the patient in proximity to the cochlea of the inner ear whereby the probe vibrations are transmitted to the cochlea to stimulate this organ and thereby alleviate the tinnitus disorder.

In this system, use is made of two adjustable audio-frequency oscillators, one operating in a low frequency range, the other operating in a high-frequency range. The outputs of these oscillators are combined and amplified to produce the complex signal applied to the probe. The mechanical vibrations transmitted by the probe in accordance with the complex signal must be properly related to the sonic frequencies of the tinnitus sounds being heard by the patient, and to this end, the patient who hears the reproduced complex signal then adjusts the frequencies of the oscillators so that the resultant complex signal acts to mask the tinnitus sounds.

The probe and diaphragm assembly includes a diaphragm defining the circular base of an acoustic horn from whose circular mouth are emitted the sounds of the complex signal reproduced by the diaphragm. Anchored on the diaphragm is a probe which extends through the circular mouth and is coaxial therewith, the probe vibrating in accordance with the signal. The diaphragm is electrodynamically actuated in accordance with the signal, so that as the cochlea of the patient's ear is subjected to these vibrations, the patient can at the same time hear the reproduced signal.

BRIEF DESCRIPTION OF DRAWINGS

For a better understanding of the invention as well as other objects and further features thereof, reference is made to the following detailed description to be read in conjunction with the accompanying drawings, wherein.

DETAILED DESCRIPTION OF INVENTION

Figure 1:
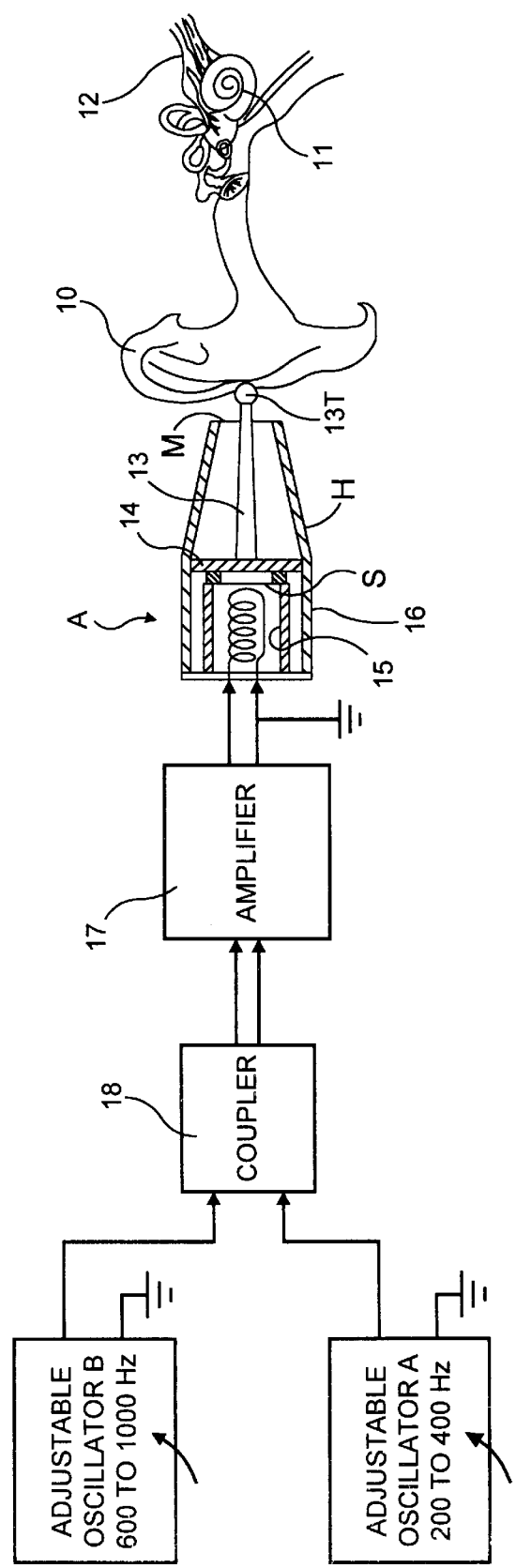
FIG. 1 is a block diagram of an electronic stimulation system in accordance with the invention for treating a patient suffering from a tinnitus disorder.

Referring now to FIG. 1 of the drawing, shown therein schematically is an ear 10 of a patient to be treated who is suffering from a tinnitus condition. The auditory system of the patient includes an inner ear provided with a cochlea 11 connected to a cochlear nerve 12 leading to the eighth cranial nerve.

The spiral ganglion of the cochlea is composed of bipolar cells, the peripheral processes of which convey auditory impulses from the specialized neuroepithelium of the inner ear which is the spiral organ of Corti, the end organ of hearing. The Corti consists of numerous hair cells aligned in rows along the 2½ turns of the cochlea.

In a system in accordance with the invention, an applicator A is provided which includes a probe 13 anchored at the center of a circular diaphragm 14 made of spring steel or similar material. Diaphragm 14 defines the circular base of a conical acoustic horn 14 whose circular mouth M has a smaller diameter than that of the base.

Probe 13 extends through mouth M of horn H and is coaxial therewith, the probe terminating in a bulbous tip T. The probe is molded of a high-strength composite material having a high degree of transmittance for sound and vibrations.

Diaphragm 14 is electrodynamically actuated by an electromagnet 15 formed by a cylindrical casing of magnetic material, such as Alnico, within which is a coil to which a signal is applied to create a magnetic field which is to be modulated in accordance with the signal.

Electromagnet 15 is housed in a cylindrical shell 16 that is joined to the base of horn H and is operatively-coupled to diaphragm 14 by natural rubber spacers S. These elastomeric spacers, while permitting the diaphragm to vibrate and thereby reproduce the tones of the complex audio signal applied to the electromagnet, act to dampen or soften these tones so that they are easier to listen to as the patient at the same time listens to internally-generated tinnitus sounds.

Applied to electromagnet 15 is a complex signal in the audio range yielded by an amplifier 17 whereby diaphragm 14 and probe 13 coupled thereto are caused to vibrate vigorously in accordance with the signal These vibrations propagated through the tissue between the probe and the cochlea act to so stimulate the cochlea so as to cause the tinnitus condition to be alleviated. With repeated treatments, the tinnitus condition will be substantially reduced or eliminated.

In practice, the probe is placed against the mastoid bone behind the earlobe, thereby causing the cochlea under the mastoid bone to receive the probe vibrations.

To generate the complex signal, two oscillators A and B are provided. Oscillator A, whose frequency is adjustable, generates a frequency in the low-frequency sonic range of about 200 to 400 Hz. Oscillator B, whose frequency is adjustable, generates a frequency in the high-frequency sonic range of about 600 to 1000 Hz. The outputs of oscillators A and B are combined in a coupler 18 which may be a resistive or capacitive network, the output of which is applied to amplifier 17. In practice, amplifier 17 may be a 10 watt amplifier whose output volume is adjustable. The complex signal yielded by the amplifier includes the low and high frequencies of the oscillators as well as the positive and negative beats of these frequencies.

In order to effectively treat the particular tinnitus condition from which patient 10 suffers, the mechanical vibrations transmitted by probe 13 to cochlea 11 which are in accordance with the complex signal, must be properly related to the sonic frequencies of the tinnitus sounds being heard by patient 10.

Since it is only the patient who hears the internally-generated tinnitus sounds, the patient himself must determine which vibratory frequencies transmitted to the cochlea by probe 13 are effective. To this end, the patient while hearing these tinnitus sounds, adjusts the settings of oscillators A and B within their respective low and high frequency sonic ranges until he finds settings at which the resultant complex signal acts to mask or interfere with the tinnitus sounds.

To carry out this operation, the volume of amplifier 17 is turned down so that the patient can clearly hear these tinnitus sound as he listens to the sounds stimulated in the cochlea by the vibrations of the probe, for the cochlea translates these vibrations into sounds. When the patient finds settings for oscillators A and B which result in a complex signal whose character is such that it interferes with or masks the tinnitus sounds, the system is then ready for treatment and the amplifier volume is then turned up for this purpose.

In order for the patient to hear the reproduced sounds of the complex signal in a normal way, that is through the outer ear, as well as by way of vibrations transmitted by the probe to the cochlea, the acoustic horn H, in conjunction with the electrodynamically-actuated diaphragm 14, acts as an electrodynamic loud speaker which clearly reproduces the complex signal. These sounds are emitted from the mouth of the horn behind the ear lobe of the patient and are picked up by the outer ear of the patient.

Each treatment is conducted for several minutes and is repeated at least twice a day until the tinnitus disorder suffered by the patient is substantially reduced or eliminated. The severity of the tinnitus disorder varies from patient to patient, hence the duration of the treatment to overcome this disorder varies from patient to patient.

PRINCIPLES OF OPERATION

As pointed out previously, a tinnitus condition is due to the artificial stimulation of particular nerve cells in the nerve center associated with the brain responsible for processing sounds, each nerve cell having an assigned frequency. Though the cause of this faulty stimulation is not known, what a patient does know is the sonic nature of these ringing or other sounds, for he hears these sounds.

The tinnitus sounds are not composed of a steady tone, but of a tone which in musical terms would be referred to as a vibrato. Thus the basic ringing tone is relatively high sonic frequency, this being modulated by a sonic tone of lower frequency. Hence the nerve cells which are artificially stimulated to produce tinnitus sounds are those nerve cells whose assigned frequencies are such as that together they recreate the ringing sounds.

In a system in accordance with the invention, the complex signal is composed of a high-frequency sonic tone modulated by a low-frequency sonic tone. This signal serves to electrodynamically actuate the probe to produce vibrations whose repetition rates correspond to the frequencies of the complex signal, which frequencies are similar to those which make up the ringing sounds.

The vibrations transmitted by the probe to the cochlea act to shock excite the nerve cells responsible for the tinnitus condition and act to restore these cells to a normal state in which the cells are subject to artificial stimulation and therefore cease to produce tinnitus sounds.

But for the system to be effective, it is essential that the patient being treated who hears the internally-generated tinnitus sounds also clearly hears the externally-generated complex signal, for only then it is possible for the patient to adjust this signal so that its complex frequencies function to mask the tinnitus sounds.

An applicator in accordance with the invention which acts as a loudspeaker for the reproduced complex signal as well as a vibrating probe renders the system effective for its intended purpose.

Figure 4:
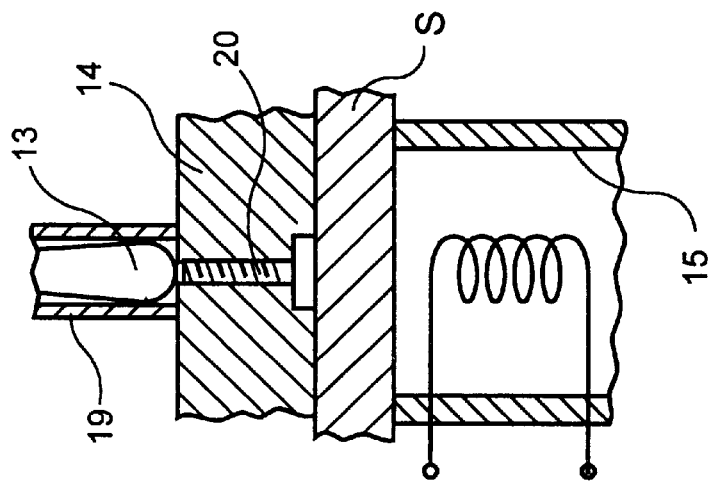
FIG. 4 illustrates how the electrode is coupled to the diaphragm of the assembly and how the diaphragm is coupled to the probe thereof.
Figure 3:
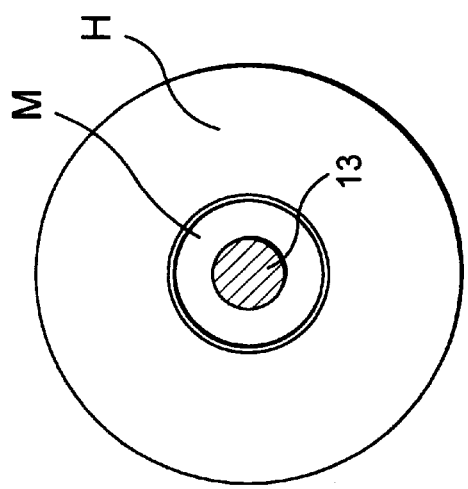
FIG. 3 is a top view of the assembly.
Figure 2:
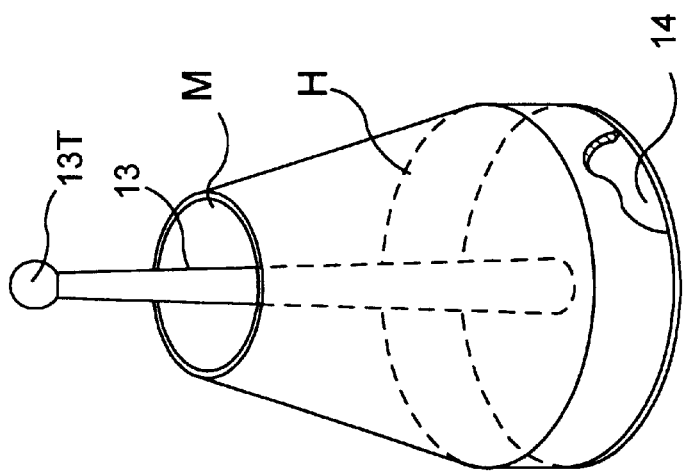
FIG. 2 illustrates the diaphragm and probe assembly included in the system.

Probe 13 is preferably anchored on steel diaphragm 14 in the manner shown in FIG. 4 in which it will be seen that the bottom end of the probe is telescoped into a mounting tube 19, and that the end of the probe is engaged by the point of a screw 20 threaded into diaphragm 20. This point contact between the probe and the diaphragm enhances the transfer of high-frequency components of the complex signal from the vibrating diaphragm to the probe.

While there has been shown and described an electronic stimulation system for treating tinnitus disorders in accordance with the invention, it will be appreciated that many changes and modifications may be made therein without, however, departing from the essential spirit thereof.

We claim:

1. An electronic stimulation system for treating a patient having a tinnitus condition in which he hears ringing or other sounds in the sonic frequency range, the sounds heard internally by the patient having predetermined frequencies in this range, said system comprising:

A. means to generate a complex electrical signal having frequency components lying within said sonic range, said means being adjustable by the patient to yield frequency components which mask the frequencies of the tinnitus sounds heard by the patient;

B. means responsive to said complex signal to produce mechanical vibrations corresponding thereto;

C. means to apply said mechanical vibrations to a site on said patient in the proximity of the cochlea whereby the vibrations are conveyed to the cochlea to relieve the tinnitus condition; and D. means to audibly reproduce the complex signal so that it can be heard by the patient as he adjusts the means to generate the complex signal to include the frequency components that mask the tinnitus sounds.

2. A system as set forth in claim 1, in which the means to generate the complex signal are constituted by a low sonic-frequency oscillator adjustable in frequency and a high sonic frequency, oscillator adjustable in frequency, and means to combine the adjusted outputs of said low and high-frequency oscillators to produce the complex signal having the masking frequency components.

3. A system as set forth in claim 2, in which the low-frequency oscillator is adjustable in a range whose upper limit is about 400 Hz.

4. A system as set forth in claim 3, in which the high-frequency oscillator is adjustable in a range whose upper limit is about 1000 Hz.

5. A system as set forth in claim 2, in which the complex signal is applied to the means to produce mechanical vibrations through an amplifier.

6. A system as set forth in claim 5, in which the amplifier is adjustable so that the volume of the reproduced complex signal, as heard by the patient, can be raised or lowered relative to the tinnitus sounds heard by the patient.

7. A system, as set froth in claim 1, in which the means to produce said mechanical vibrations and the means to audibly reproduce the complex signal are constituted by an electrodynamically-actuated diaphragm mounted at the base of a conical horn having a circular mouth, and a probe anchored on the diaphragm and extending axially through the mouth, the probe vibrating in accordance with the signal and the diaphragm in combination with the horn acting as a loud speaker to reproduce the complex signal.

8. A system as set forth in claim 7, in which the probe is formed of high-strength, synthetic plastic material.

9. A system as set forth in claim 7, in which the diaphragm is formed of spring steel.

10. The system of claim 1, wherein the system is applied through the outer ear.

* * * * *